United States Patent
Garton, Jr.

(10) Patent No.: US 6,361,314 B1
(45) Date of Patent: Mar. 26, 2002

(54) ORTHODONTIC BRACKET

(75) Inventor: Robert E. Garton, Jr., Elkhart Lake, WI (US)

(73) Assignee: American Orthodontics, Sheboygan, WI (US)

( * ) Notice: Subject to any disclaimer, the term of this patent is extended or adjusted under 35 U.S.C. 154(b) by 0 days.

(21) Appl. No.: 09/843,670

(22) Filed: Apr. 27, 2001

Related U.S. Application Data

(60) Provisional application No. 60/200,320, filed on Apr. 28, 2000.

(51) Int. Cl.$^7$ ................................................. A61C 3/00
(52) U.S. Cl. ............................................................ 433/8
(58) Field of Search ............................. 433/8, 9, 10, 24

(56) References Cited

U.S. PATENT DOCUMENTS

| | | | | |
|---|---|---|---|---|
| 3,922,787 A | * | 12/1975 | Fischer et al. | 433/8 |
| 4,337,037 A | * | 6/1982 | Kurz | 433/8 |
| 4,531,911 A | * | 7/1985 | Creekmore | 433/8 |
| 4,842,512 A | * | 6/1989 | Kesling | 433/8 |
| 5,067,897 A | * | 11/1991 | Tuneberg | 433/8 |
| 5,125,832 A | * | 6/1992 | Kesling | 433/8 |

* cited by examiner

Primary Examiner—Nicholas D. Lucchesi
(74) Attorney, Agent, or Firm—Philip G. Meyers Intellectual Property Law, P.C.

(57) ABSTRACT

The invention provides an orthodontic bracket having a base portion configured for attachment to a mounting device such as a bonding pad that is directly secured to the tooth of a patient. A central portion of the bracket adjacent the base portion has a pair of sides that taper to a minimum diameter at a midline of the central portion, preferably giving the bracket an hourglass shape. A pair of single tie wings extend in gingival and occlusal directions respectively from the central portion, which tie wings define outer end portions that are wider than the central portion and have undersurfaces positioned for mounting archwire retaining bands therein. An outwardly opening archwire slot elongated in the mesial direction is formed in the central portion, which slot extends at an acute angle relative to an imaginary line extending in a buccal-lingual direction such that the slot opens closer to the gingival tie wing than the occlusal tie wing. An inner end portion of the occlusal tie wing overhangs the archwire slot. This bracket has a simple shape yet provides optimum interbracket distance as described hereafter, which distance is especially important when an orthodontic appliance using the bracket is to be mounted on the lingual side of the teeth where the curvature of the archwire is more severe.

3 Claims, 2 Drawing Sheets

ORTHODONTIC BRACKET

RELATED APPLICATIONS

This application is a conversion of provisional application Ser. No. 60/200,320, filed Apr. 28, 2000, the disclosure of which is incorporated herein by reference for all purposes.

TECHNICAL FIELD

The present invention relates to orthodontic brackets specifically designed for use on the lingual side of the teeth.

BACKGROUND OF THE INVENTION

Orthodontic brackets for use on the lingual (back) side of the teeth are generally known but have not found the wide application that standard, buccal-side mounted brackets have seen. One such bracket is described in FIGS. 18–21 of Creekmore U.S. Pat. No. 4,531,911. Creekmore teaches a single/twin orthodontic bracket with an elastic ligature member securing an edgewise archwire within the archwire slot of the bracket wherein the archwire slot and archwire are severely angulated position such as for lingual application. The Creekmore bracket has four separate tie wings and a complicated profile that makes it difficult to use and manufacture. The present invention provides an improves, simplified lingual bracket having an angles slot.

SUMMARY OF THE INVENTION

The invention provides an orthodontic bracket having a base portion configured for attachment to a mounting device such as a bonding pad that is directly secured to the tooth of a patient. A central portion of the bracket adjacent the base portion has a pair of sides that taper to a minimum diameter at a midline of the central portion, preferably giving the bracket an hourglass shape. A pair of single tie wings extend in gingival and occlusal directions respectively from the central portion, which tie wings define outer end portions that are wider than the central portion and have undersurfaces positioned for mounting archwire retaining bands therein. An outwardly opening archwire slot elongated in the mesial direction is formed in the central portion, which slot extends at an acute angle relative to an imaginary line extending in a buccal-lingual direction such that the slot opens closer to the gingival tie wing than the occlusal tie wing. An inner end portion of the occlusal tie wing overhangs the archwire slot. This bracket has a simple shape yet provides optimum interbracket distance as described hereafter, which distance is especially important when an orthodontic appliance using the bracket is to be mounted on the lingual side of the teeth where the curvature of the archwire is more severe.

Such a bracket may be used to form an orthodontic appliance according to the invention applied to the lingual side of a patient's teeth. The appliance includes a number of such brackets each mounted to lingual surfaces of incisor or canine teeth of the patient, united by a mesial archwire positioned in the archwire slot of each bracket and retained therein by elastic bands mounted over the tie wings and securing the archwire to each bracket. These and other aspects of the invention are discussed further in the detailed description which follows.

DETAILED DESCRIPTION

Figure 1:
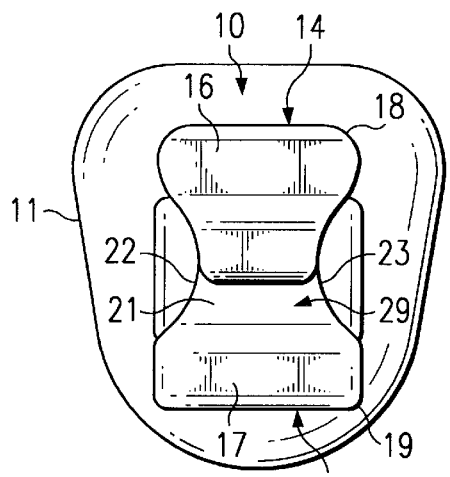
FIG. 1 is a top view of a universal anterior bracket according to the invention.
Figure 2:
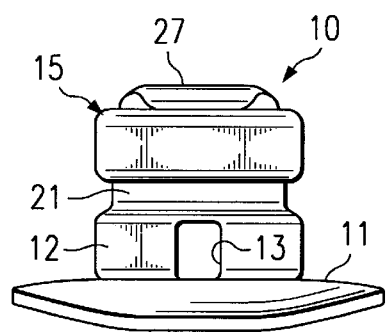
FIG. 2 is an end view of the bracket of FIG. 1 looking through the gingival slot.

A dental appliance according to the invention includes a plurality of anterior and bicuspid brackets according to the invention mounted on the lingual side of the patient's teeth on an archwire and ligated to the archwire with elastic bands. Referring to FIGS. 1–4, an anterior bracket 10 according to the invention for mounting to upper and lower canine and incisor teeth is shown bonded to a mounting pad 11. A central, generally rectangular base portion 12 of bracket 10 has a vertical slot 13 running therethrough. A pair of occlusal and gingival wings 14, 15 extend in occlusal and gingival directions. Wings 14, 15 have a pair of generally rectangular end portions 16, 17 with rounded inner and outer corners 18, 19 as shown. A central, hourglass-shaped portion 21 of bracket 10 united the ends 16, 17 and defines the tie wings. A pair of sides 22, 23 on opposite sides of central portion 21 each have a concave shape in the occlusal-gingival direction, giving central portion 21 its preferred hourglass shape. Sides 22, 23 are of uniform cross-section when viewed as shown in FIG. 1.

Figure 3:
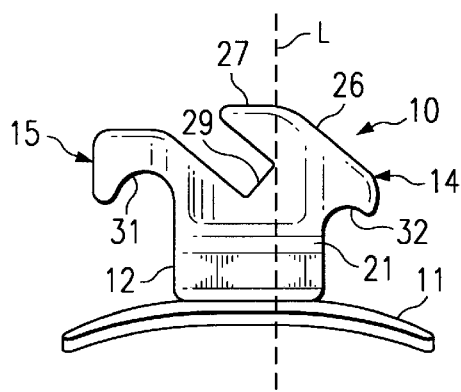
FIG. 3 is a lateral (side) view of the bracket of FIG. 1.
Figure 4:
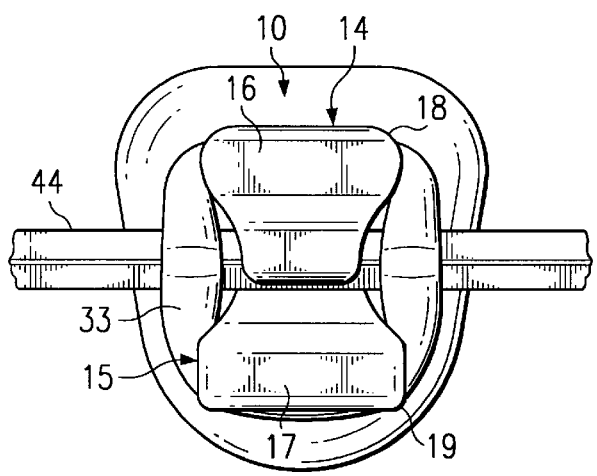
FIG. 4 is a top of view of the bracket of FIG. 1 ligated to an archwire.
Figure 5:
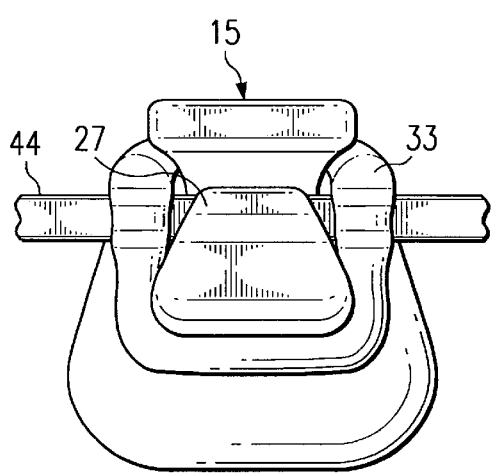
FIG. 5 is a occlusal perspective view of the bracket of FIG. 4.

As shown is FIG. 3, occlusal wing 14 has a different shape from gingival wing 15. Wing 14 has a outwardly, sloped shoulder 16 leading to an overhanging inner end portion 27 in which the highly angled archwire slot 29 is formed. Slot 29 extends in the mesial direction, is preferably rectangular in cross-section and set at an angle in the range of 30 to 50 degrees relative to an imaginary buccal-lingual line L perpendicular to the surface of the tooth and bonding pad 11. Wing 15 which is proximate the opening of slot 29 lacks an angled shoulder and overhanging portion and defines a rounded undercut 31 for mounting the ligature band 33. Undercut 31 is slightly higher (further our from the tooth surface) than corresponding undercut 32 beneath wing 14.

In general, the hourglass configuration of this embodiment can be either symmetrical or asymmetrical as tooth anatomy dictates, permitting greater flexibility in the use of the system. The hourglass or similarly narrowed shape of the tie wings and central portion of the bracket makes the archwire slot shorter in comparison to known brackets designed for a similar purpose, resulting in a greater open space (interbracket distance) along the archwire when a series of these brackets are mounted to the teeth. This increases both effective working length and tooth movement efficiency of the archwire. The relatively wide tie wings aid in rotational control during treatment, and the vertical slot 13 lingual to the archwire slot bounded on one side by pad 11 further facilitates tooth movement by the selective placement specific auxiliary components designed by the clinician.

Figure 6:
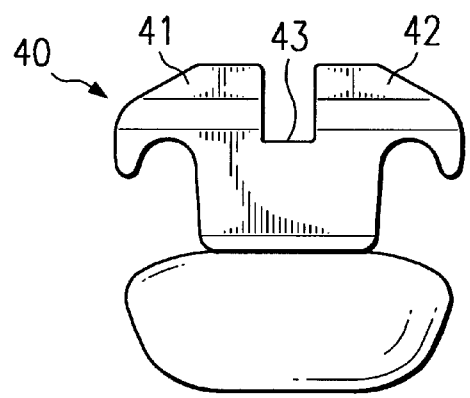
FIG. 6 is a side view of a bicuspid bracket for use in the system of the present invention.
Figure 7:
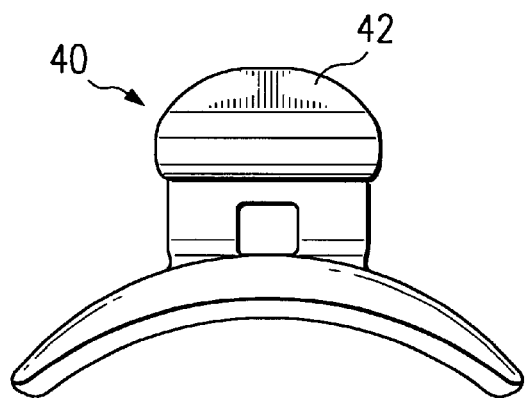
FIG. 7 is a top (end) view of the bracket of FIG. 6, looking through the archwire slot.
Figure 8:
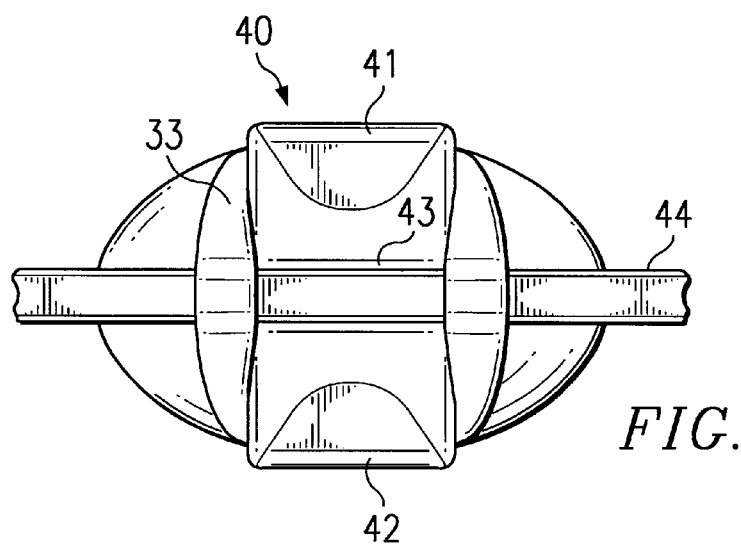
FIG. 8 is the bracket of FIG. 6, ligated to an archwire.

FIGS. 6–8 illustrate a bicuspid bracket 40 for use in an orthodontic appliance according the to invention. Bracket 40 may be a conventional lingual bracket with symmetrical tie wings 41, 42 and a non-angled archwire slot 43. A combination of an archwire 44, brackets 10, 40 and elastic bands 33 are used to create a lingual orthodontic appliance according to the invention in a manner that will be appreciated by the skilled clinician.

Although embodiments of the invention have been illustrated in the accompanying drawing and described in the foregoing detailed description, it will be understood that the invention is not limited to the embodiments disclosed but, as will be appreciated by those skilled in the art, is susceptible to numerous modifications and variations without departing from the spirit and scope of the invention as hereinafter claimed.

What is claimed is:

1. An orthodontic bracket, comprising:
    a base portion configured for attachment to a mounting device directly secured to the tooth of a patient;
    a central portion adjacent the base portion, which central portion has a pair of sides that taper to a minimum diameter at a midline of the central portion;
    a pair of single tie wings which extend in gingival and occlusal directions respectively from the central portion, which tie wings define outer end portions wider than the central portion and have undersurfaces positioned for mounting archwire retaining bands therein; and
    an archwire slot elongated in the mesial direction is formed in the central portion, which slot extends at an acute angle relative to an imaginary line extending in a buccal-lingual direction such that the slot opens closer to the gingival tie wing than the occlusal tie wing, and an inner end portion of the occlusal tie wing overhangs the archwire slot.

2. The bracket of claim 1, wherein the sides that taper to a minimum diameter at a midline of the central portion are concave, giving the central portion and tie wings an hour-glass shape.

3. An orthodontic appliance adapted to be applied to the lingual side of a patient's teeth, comprising a plurality of brackets as claimed in claim 1 each adapted to be mounted to incisor or canine teeth of the patient, united by a mesial archwire positioned in the archwire slot and retained therein by elastic bands mounted over the tie wings and securing the archwire to each bracket when installed on said patient's teeth.

* * * * *